United States Patent [19]
Lichstein

[11] Patent Number: 5,658,270
[45] Date of Patent: Aug. 19, 1997

[54] BODY ADHERING SANITARY PROTECTION PRODUCTS

[75] Inventor: Bernard M. Lichstein, Elizabeth, N.J.

[73] Assignee: McNeil-PPC, Inc., Skillman, N.J.

[21] Appl. No.: 427,011

[22] Filed: Apr. 24, 1995

[51] Int. Cl.$^6$ .............................. A61F 13/15; A61F 13/20
[52] U.S. Cl. .................. 604/387; 604/372; 604/355.1; 604/386; 602/54
[58] Field of Search .................. 604/307, 358, 604/365, 372, 378, 385.1, 386–387; 602/54–56

[56] References Cited

U.S. PATENT DOCUMENTS

| | | | |
|---|---|---|---|
| 2,399,545 | 4/1946 | Davis | 602/59 |
| 2,742,903 | 4/1956 | Lightner | 604/385.1 |
| 2,929,379 | 3/1960 | Poulsen | 604/372 |
| 2,940,868 | 6/1960 | Patchell | 602/55 |
| 4,064,880 | 12/1977 | Logan . | |
| 4,484,919 | 11/1984 | Sohn et al. . | |
| 4,554,191 | 11/1985 | Korpman . | |
| 4,576,597 | 3/1986 | Hlaban | 604/389 |
| 4,596,244 | 6/1986 | Jackson | 604/389 |
| 4,753,648 | 6/1988 | Jackson | 604/389 |
| 4,982,450 | 1/1991 | D'Huissier . | |
| 5,114,419 | 5/1992 | Daniel et al. . | |
| 5,308,313 | 5/1994 | Karami et al. | 602/54 |
| 5,391,161 | 2/1995 | Hellgren | 604/366 |
| 5,429,631 | 7/1995 | Grenier | 604/378 |
| 5,445,627 | 8/1995 | Mizutani et al. | 604/389 |

FOREIGN PATENT DOCUMENTS

| | | |
|---|---|---|
| 0199857A1 | 11/1986 | European Pat. Off. . |
| 0228353 | 7/1987 | European Pat. Off. ............. 604/358 |
| 0518291A1 | 12/1992 | European Pat. Off. . |
| 0638302A1 | 2/1995 | European Pat. Off. . |
| 3535547A1 | 4/1987 | Germany . |
| H6-9622 | 2/1994 | Japan ................. 604/386 |
| 2284767 | 6/1995 | United Kingdom . |
| WO91/01702 | 2/1991 | WIPO . |
| WO95/16424 | 6/1995 | WIPO . |
| WO96/13238 | 5/1996 | WIPO . |

*Primary Examiner*—P. Zuttarelli

[57] ABSTRACT

Provided are absorbent sanitary protection products for direct attachment to the skin and hair of a user. The products comprise an absorbent core, a barrier layer coupled to one side of the core and a pressure sensitive adhesive layer on the side of the core that faces the body of a user. The pressure sensitive adhesive has sufficient adhesive strength to enable the product to adhere securely to the skin and hair of the user and yet to be removed without pain or trauma. Products described include those that are restricted to covering and adhering to the perineal area as well as those having ancillary structures to attach to body structures beyond the perineal area. Additionally disclosed is a packaged arrangement of the products of the invention for which little or no release paper is required.

27 Claims, 3 Drawing Sheets

BODY ADHERING SANITARY PROTECTION PRODUCTS

BACKGROUND OF THE INVENTION

This invention relates to sanitary protection products, and more particularly, to body adhering panty shields, sanitary napkins, incontinence devices and the like. In accordance with this invention, products are provided wherein a pressure sensitive adhesive is placed on body contacting surfaces of the product, to permit its attachment directly to the hair and/or skin of the user, rather than to an undergarment.

Sanitary protection products, such as panty shields, sanitary napkins, incontinence devices and the like have heretofore conventionally been attached to the body of a user by mechanical means, such as belts, and assisted by attachment means such as pins and hooks. Products requiring adhesive tapes, velcro tapes, spring-like clasps and flaps have also been proposed. Most recently, and for some years, products have been attached to the crotch of the user's undergarment by means of pressure sensitive adhesive strips and patches on a surface of the product that faces away from the user's body and toward the inside of the undergarment and by adhesive and mechanical flaps that envelop the panty crotch. Adhesive is currently the most widely used means of attachment. However, the effectiveness of such conventional means is limited by distorting, shearing and conflicting movements of the undergarment and body, which distort the product and cause it to move away from a position in which it is able to reliably and intimately contact the body. These distorting, shearing and conflicting movements can occur between different parts of the body, as with the highly mobile opposite motions of each of the buttocks and of the thighs relative to themselves and relative to the less mobile structures of the perineal areas such as the vulva and labia.

Distorting, shearing and conflicting movements and forces also occur as a result of relative movement between the body and the panty. This is especially aggravated when the panty is loose fitting, thereby exerting a pulling away from the body in addition to the distorting and conflicting forces of the panty in directions backward, forward and sideways while the body moves in somewhat opposite backward, forward and lateral directions.

Additionally, adhesives which have been used to attach known devices to undergarments are often sufficiently aggressive to leave residues on the undergarment and at times to tear the undergarment on removal. Also, at times, insufficient adhesive is available to keep the product attached to the area of initial attachment to the undergarment or to keep the product attached at all to the undergarment during the period of use.

It has now been found, unexpectedly, that the body contacting surface of sanitary protection products such as panty shields, sanitary napkins, incontinence devices and the like can be coated with a light deposit of a pressure sensitive adhesive so as to create a body-attachable product that is easy to apply directly and intimately to skin or to hair; does not fall off during vigorous activity and body movement or when the user is sitting on the toilet; is comfortable to wear; be reattached; and is painless and otherwise atraumatic to remove. It has further unexpectedly been found that such products can be made so that they exhibit the above-described desirable attachment, wear, use and removal properties whether attached to skin or to hair. For the purpose of this disclosure panty shields and sanitary napkins will be used as examples. It has still further unexpectedly been found that the design of the products of this invention, as well as the design, nature and amount of adhesive used in the body facing adhesive coating of the products of this invention, permit the elimination of most, if not all, of the adhesive-protecting release papers customarily used in such products.

It is not necessary to attach the products of this invention to an article of clothing such as a panty or pantyhose. In fact, the products of this invention can be worn without undergarments and certainly with sports garments such as exercise suits and swimsuits. It has also unexpectedly been found that products in accordance with this invention can be made to fit so closely to the body that the effect of interanatomic movements and of movements between the body and clothing are minimized. This close fit and lack of movement minimizes the tendency of the product to bunch up, rope, twist or otherwise distort. Products of this invention, being worn quite close the sources of body liquids, the liquids being comprised mainly of menses, urine and perspiration, are most likely to intercept and absorb the liquids before they can escape beyond the product's confines. Thus leakage protection and comfort are maintained and even enhanced.

Products in accordance with this invention are easy to apply, attach directly and intimately to the body, tend to stay securely in place and do not distort during use. Moreover, they are comfortable to wear and painless to remove. They do not pull the pubic hair nor do they irritate the skin.

Such products are also simpler in construction and often smaller than traditional panty shields or sanitary napkins. Since they adhere so intimately to the body, there is less need in their structure for extra absorbent areas and exaggerated shapes or for additional elements such as attachment wings and tabs, elastic curving and shaping means, leakage protecting cuffs and resilient and deformation resisting elements. Some designs, as discussed above, in accordance with the invention do not require release paper to protect the adhesive on the body contacting surface, thereby providing distinct economic, operational, environmental and use advantages. Some panty shields and sanitary napkin designs of this invention do not require a separate cover element for the absorbent core, since the adhesive coating and in some instances binders within the core provide sufficient mechanical integrity and abrasion resistance for the surface of the core. The result is a low cost product that fits close to the body and has little tendency to shift or bunch up during wear.

The above and other objects and advantages of the invention will be apparent from the following description.

SUMMARY OF THE INVENTION

The above and other objects of the present invention are realized, in a presently preferred form of the invention, by a sanitary protection product which comprises an absorbent core, preferably affixed to a barrier ply which prevents leakage of liquids that have been absorbed by the surface of the core that faces the user and have reached the opposite surface. The core may be comprised of conventional adsorbents such as wood pulp or sphagnum moss, superabsorbents or simple or composite or layered non-woven fabric structures, as are known to those skilled in the art. The adsorbents may be combined as homogeneous mixtures, heterogeneous mixtures, composite or layered structures, where the layered structures may also be comprised of gradients of materials and/or degrees of porosity and density, as are known to those skilled in the art. If the product is a panty shield or sanitary napkin which is customarily covered with a perforate cover, the face of the core that faces the body of the user may have affixed to it a transfer layer, typically of a nonwoven structure, to facilitate transfer and distribution of liquid from the cover to the core. It has surprisingly been found that such a layer may be omitted in devices in accordance with this invention, since liquid has immediate access to the core, not being hindered by the presence of a covering material. However when a product has a cover, a transfer layer may be necessary to help liquid penetrate the cover and be transferred to the core below. The body facing surface of the product may be covered with a cover typically comprised of a nonwoven fabric or an apertured film. When a cover is used in this invention, the body facing adhesive layer is then disposed on the outside body facing side of the cover.

The barrier layer can be made of films comprised of polymers or of composites and/or laminates of such polymers. The barrier layer can be made of commonly used films, such as polyolefins. Other films such as polyurethanes, polyamides and polyesters can also be used. However, because of the close fitting quality of the napkins of this invention, it is may be desirable, but not necessary, to use breathable films that permit moisture vapor and air to transfer easily across the barrier without permitting fluid to cross the barrier. This may provide a product that is cool and comfortable to wear. Examples of such films, without being restrictive, are polyurethanes and microporous films which may be formed by stretching, leaching out of soluble included substances, and the like. Breathability may also be introduced by forming the body contacting surface of the product or the entire product into a three dimensional structure that allows air to circulate. Corrugated and embossed surfaces or cup-like or otherwise curved product structures are examples of such three dimensional structures.

In accordance with this invention, a layer of pressure-sensitive adhesive, preferably discontinuous or forming a pattern, according to the needs of the particular product design, is associated with the face of the core facing the body of a user. The adhesive is of sufficient adhesive strength to enable the product to adhere to the skin or hair of the user, but is of such character that the product can be removed without pain or trauma to the user. It has been found that in some embodiments of the invention, suitable pressure sensitive adhesives can successfully be used at coating weights as little as 0.5 to 1.5 milligrams per square inch.

Pressure sensitive adhesives that are not overly tacky and do not have excessive cold flow and creep can be used to good advantage in the present invention. The preferred chemical nature of these adhesives and their formulation is one that offers relatively low skin irritation potential, no skin sensitization potential and are resistant to oxidation. So called "hypoallergenic" adhesives, such as the polyacrylates, that have little or no potentially irritating antioxidants added are preferred. These adhesives also have relatively good wet stick properties.

In one of its basic and simple aspects, the present invention provides an absorbent product, such as a panty shield or sanitary napkin, capable of direct attachment to the skin and hair of the perineal area or of anatomic structures peripheral to the perineum, such as the suprapubic abdominal area, the creases forming the junctions between the perineum and the insides of the thighs, the posterior fourchette (area between the posterior labial commissure and the anus) and the buttocks.

Devices in accordance with the invention can also, if desired, be configured with ancillary attachment means, such as tabs or wings adhesively coated on their respective body contacting surfaces. Such attachment means can preferably be made to attach to relatively hairless parts of the body of a user, such as the abdomen, the buttocks, the posterior fourchette region and the creases forming the junctions between the perineum and the insides of the thighs.

The design of the products of this invention and the design, nature and amount of adhesive used on the body facing surface of this invention, allows several products to be packaged together without additional adhesive-protecting release liners. Thus, the adhesive coated surface of one product can be put against the barrier layer of another product and, later, removed without tearing the barrier layer of the second product. Therefore, devices in accordance with this invention may be packaged, adhesive-coated surface-to-barrier surface with only the last, unprotected product requiring release paper. Thus, the products of this invention can permit the elimination of most, if not all, of the adhesive-protecting release liners customarily used in such products.

BRIEF DESCRIPTION OF DRAWINGS

There are shown in the drawings aspects of certain preferred embodiments, it being understood that the invention is not limited to the precise arrangements and instrumentalities shown.

DETAILED DESCRIPTION

Figure 1:
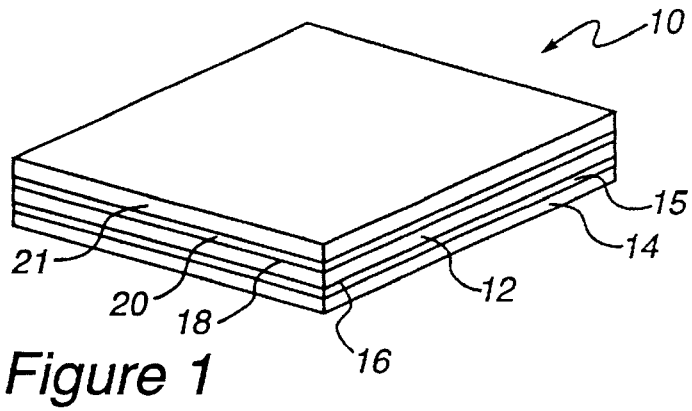
FIG. 1 is a perspective view of a portion of a sanitary protection product in accordance with the invention.

Referring now to the drawings in detail, wherein like reference numerals indicate like elements, there is seen in FIG. 1 a portion of a sanitary protection product in accordance with this invention. The sanitary protection product, which can take the form of a panty shield, sanitary napkin, or the like, is designated generally by the reference numeral 10. The sanitary protection product 10, which is intended to be attached directly to the skin and/or hair of the user, comprises an absorbent core 12, provided with a barrier ply 14. The barrier ply 14 is coupled by means of a layer of adhesive 15 to the core 12 on a side 16 of the core which would normally be disposed away from the body of a user of the product 10.

On the side 18 of the core 12 facing the body of a user and disposed to contact the body of the user is a layer of pressure sensitive adhesive 20 which will be described in greater detail below. The adhesive 20 has sufficient adhesive strength to enable the product 10 to adhere securely to the skin and/or hair of the user and to be removed without pain or trauma to the user. The adhesive 20 is optionally covered and protected until use with a layer of release paper 21, whose release characteristics may be imparted by means such as applying silicone-based substances.

Exemplary products were made from laminated structures comprised of two layers of material and two layers of adhesive, a core 12 as mentioned above, and a barrier ply 14.

The core 12 and barrier ply 14 were pre-sprayed entirely on one side with an adhesive 20 comprised of National Starch Hotmelt adhesive 5539, a styrene butadiene styrene adhesive, at weights ranging from 0.5 to of 4 milligrams per square inch, the core 12 being sprayed on its body-facing surface 18, with the adhesive 20. The core 12 consisted of James River Airtex 352, an absorbent material made of wood-pulp and a binder of about 15% ethylene vinyl acetate copolymer. This core 12 was disposed with its above-mentioned adhesive coating 20 facing upward, so as to provide the adhesive layer 20 facing the body of a user. The adhesive layer 20 was covered and protected until used with a layer of release paper 21, coated with silicone on the adhesive facing side for easy release from adhesive 20.

The barrier ply 14 was a polyethylene barrier, consisting of Edison Plastics RT/EVA 456, which has ethylene vinyl acetate on one side, here the side to which an adhesive 15 was adhered, which in turn was adhered to the non-adhesive side of the core 12.

It has been found that with some absorbent cores, such as the core 12 in the embodiment seen in FIG. 1, it is practical to dispense with a transfer layer, since the core itself efficiently transfers, distributes and retains liquid. Since there is no cover in this embodiment, a transfer layer is not as necessary. A transfer layer may be necessary, however, when a cover is present, to pull liquid through the cover and transfer it to the core below, as is explained above. It has also been found that with some cores, such as core 12, it is practical to dispense with a cover, since adhesive coating 20 lends sufficient abrasion resistance to the body facing surface 18 of core 12.

Figure 2:
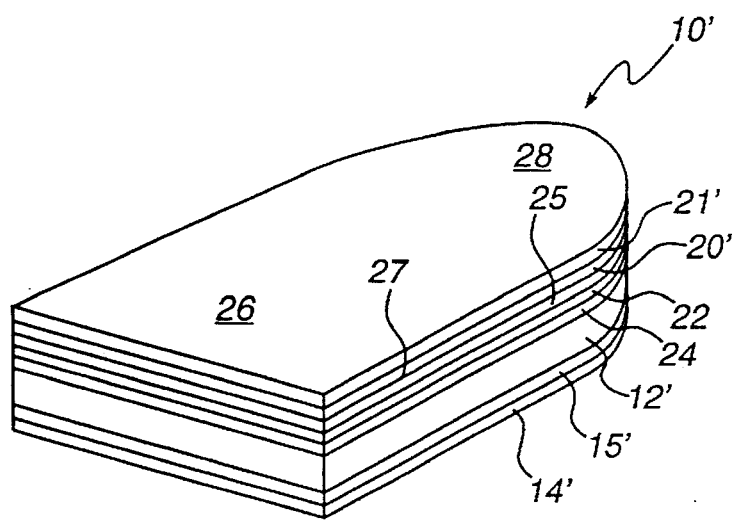
FIG. 2 is a perspective view of an embodiment of a sanitary protection product in accordance with the invention.

Referring now to FIG. 2, there is seen an embodiment of a sanitary protection product, designated generally by the reference numeral 10', similar in some respects to the embodiment shown in FIG. 1, and wherein elements corresponding to those previously described are identified by like primed (') reference numerals. The product 10' which is, specifically, a panty shield or sanitary napkin, is adapted to be adhesively secured to the body of a user. In the embodiment shown in FIG. 2, a transfer layer 24, a fluid penetratable adhesive 22, and a perforate cover 25 are sequentially applied over the core 12', to provide for the core's increased abrasion resistance, improved liquid transfer and increased absorbent capacity. In this embodiment, the body-contacting adhesive 20' is necessarily disposed on the body facing surface 27 of cover 25. However, the product of FIG. 2 can be of a layered construction similar to FIG. 1 where the transfer layer 24, fluid penetratable adhesive 22 and perforate cover 25 are eliminated. Again, an optional release paper 21" may cover and protect the adhesive 20' until use.

Still referring to FIG. 2, the invention will be described in relation to product 10' which is specifically a panty shield or sanitary napkin, adapted to be adhesively secured to the body of a user.

The product 10' is so shaped as to include a generally rectangular main portion 26, from which there projects a tapered tip portion 28. The construction of product 10' may be as described above in connection with product 10. In general, product 10' may be attached to the perineal area or to anatomic structures immediately peripheral to the perineum, such as the suprapubic abdominal area, the creases forming the junctions between the perineum and the insides of the thighs, the posterior fourchette (area between the posterior labial commissure and the anus). Preferably, the product 10' covers substantially the entirety or a major portion of the perineum of the user.

The adhesive 20' preferably coats all or part of the perineum-contacting part of the product. In such an embodiment, the adhesive is preferably a discontinuous coating, as may be obtained by spraying or by printing, such as by gravure or screen printing. Discontinuities in the coating allow liquids such as menses, urine and perspiration to pass through the perforate cover 25 and into the absorbent components of the products.

Figure 5:
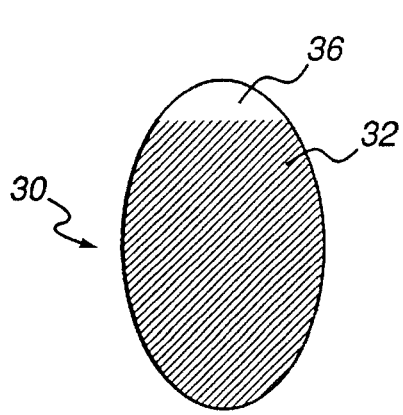
Figure 6:
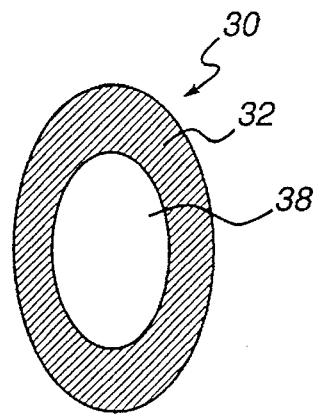
Figure 7:
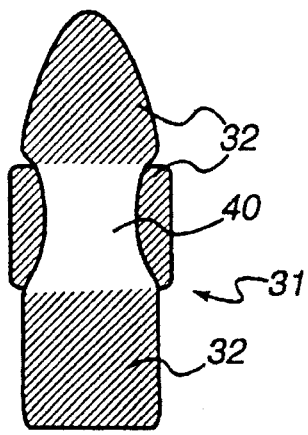

Examples of patterns of adhesive placement are shown in FIGS. 3–6 in relation to exemplary sanitary protection products 30 of generally elliptical shape, and in FIG. 7 in relation to a product 31 of irregular shape.

Figure 3:
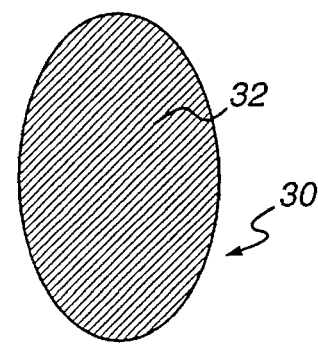
FIGS. 3–7 are plan views of the adhesive coatings on the body facing surface of the sanitary protection products in accordance with this invention.
Figure 4:
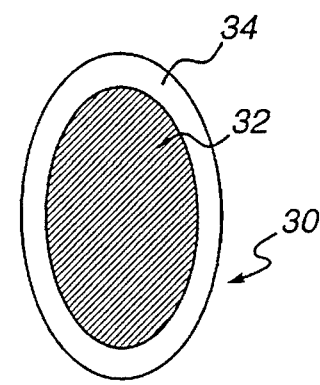

The coating of adhesive, here designated generally by the reference numeral 32, can be entirely over the body contacting surface, as shown in FIG. 3. It can also be restricted to part of the surface as shown in FIGS. 4 to 7, having the adhesive restricted to only the perimeter or to part of it as shown in FIGS. 6 and 7, or to part or all of a central portion, leaving uncoated all or part of the perimeter, as shown in FIGS. 4 and 5. An advantage of leaving at least some part of the perimeter uncoated, as at 34 in FIG. 4 and 36 in FIG. 5, is to make it easy to grasp the product at an uncoated end to apply it, and, more important, to remove it. An advantage of leaving some part of the central portion 42 uncoated as at 38 in FIG. 6 and 40 in FIG. 7, is to permit more ready fluid acceptance and transfer.

Adhesive to be applied to the anatomic structures peripheral to the perineum can be as either a continuous or discontinuous coating. In all instances the adhesive is preferably applied at a low "add-on", wherein the degree of add-on is dictated by the continuity of the coating as well as the physical properties of the adhesive. A continuous coating requires less add-on than does a discontinuous coating to achieve comparably adequate adhesion properties as well as atraumatic removal properties. A discontinuous coating, however, is preferred because the intermittent contact between the adhesive and hair or skin makes the product easier to remove, and permits air and water vapor to transpire, thereby enhancing wearing comfort, and permits liquid to pass through to the absorbent before liquid can reach the edges of the product.

The pressure sensitive adhesives in accordance with this invention have the correct and appropriate combination of an extremely low-add on and a balance of physical properties wherein they provide gentle but sufficient tack for secure attachment to hair and skin and yet release atraumatically on pulling the product away from the body. The extremely small amount of adhesive add-on is preferably just sufficient for attachment, but insufficient for intimate coating of skin and encapsulation of hair. The adhesive properties and degree of add-on also minimize the trauma anticipated from repeated removal and attachment to the same area.

Because of the closeness of the product to the body, the amount of product beyond the posterior labial commissure should be narrowed so that it interacts and is perturbed as little as possible by the presence and movement of the buttocks. In fact for certain products such as panty shields the area of product beyond the posterior labial commissure can be entirely or almost entirely eliminated.

Figure 8:
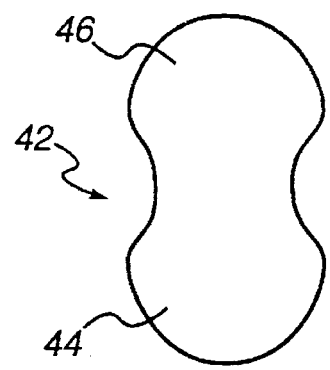
FIGS. 8 to 14 are plan views of embodiments of sanitary protection products in accordance with this invention.
Figure 9:
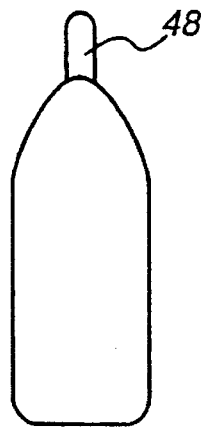
Figure 10:
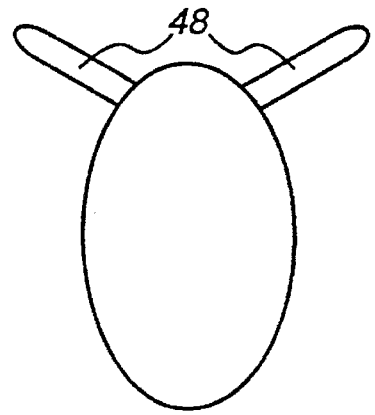
Figure 11:
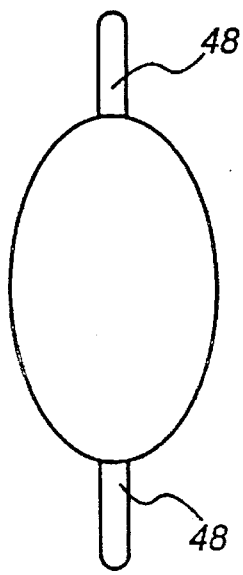
Figure 12:
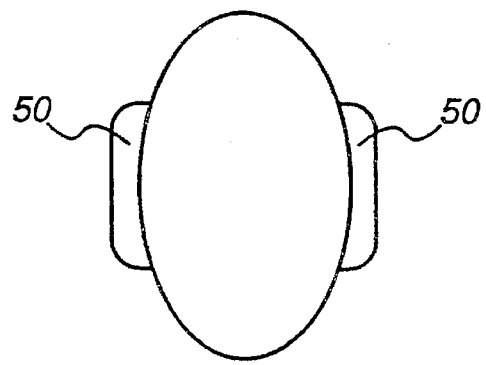
Figure 13:
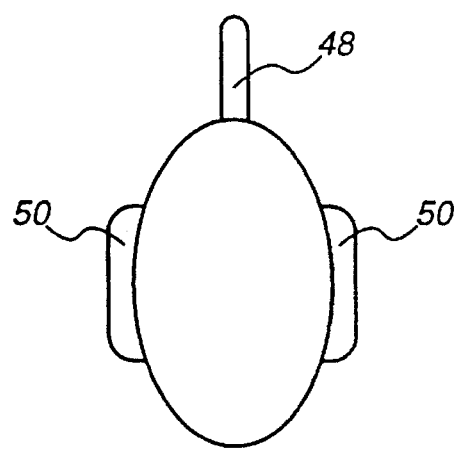
Figure 14:
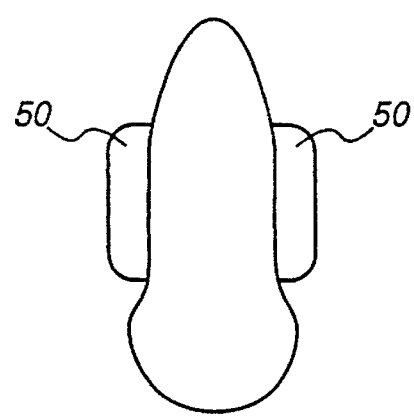

FIG. 8 shows an example of such a form of the invention, designated generally by the reference numeral 42, which covers the entirety of the perineum, but little else. The rearward portion 44 of the product 42 covers the posterior labial commissure, but is of sufficiently limited length and width to minimize contact with the buttocks of a user. The forward portion 46 of the product 42 similarly is limited to just adequately cover the anterior labial commissure. The product 42 is also similarly limited in width so as minimize contact with the inside of the thighs. A maximum width of 3 in. is suggested. A preferred maximum width is 2.5 in. A most preferred maximum width is 2.25 in. Ideally, the product 34 extends beyond the above described boundaries of the perineum by about 0.5 inches. Other examples of such products providing minimal coverage are shown in FIGS. 3 to 6 and 10 to 12.

Shapes other than the specific shapes seen in FIGS. 3 to 8 are within the purview of the invention, and may occur to those skilled in the art.

Adhesive coated perineum-contacting products of this invention are preferred because of their simplicity of manufacture, low cost and ease of use. Such designs have been found to be remarkably easy to use and remove, and function well in terms of leakage protection, comfort and staying in place. However, even if the body contacting coated surface is covered partially or completely with adhesive, it may be desirable or necessary in certain use situations to provide ancillary adhesive attachment means. This may occur when additional security is required or the product is overly large or heavy or if the anticipated fluid discharge is overly heavy. In such situations, it may be desirable to replace or augment the adhesive on the face of the product with adhesively coated ancillary attachments. These can take the form, as shown in FIGS. 9 to 14, of tabs 48 and wings 50, adhesively coated on at least part of their body contacting surfaces, which can be preferably attached to relatively hairless parts of the body such as any or all of the following: the abdomen, the buttocks (preferably to the midpoints of the globes of the buttocks), the posterior fourchette region between the posterior commissure and the anal opening, the creases forming the junctions between the perineum and the insides of the thighs. Such tabs and wings may be partially or completely coated with adhesive on their body contacting sides.

In FIGS. 9, 10, 13 and 14, in which the products do not have identical transverse ends when viewed longitudinally, the products are meant to be worn with the upper portion in each figure disposed posteriorly, toward the buttocks, and the lower portion in the figure anteriorly, toward the abdomen.

The coating weight of adhesives 20, 20', 32 of this invention, attached in use directly to hair and/or to skin, should be kept as low as possible to achieve the requisite balance between adequate, but not aggressive, adhesive attachment, and easy, painless and otherwise atraumatic removal and reapplication to the same anatomic areas. A range of weights useful for this invention is 0.5–15 mg/in$^2$, with a preferred range of 0.5–10 mg/in$^2$ and with a most preferred range of 0.5–5 mg/in$^2$. Specific preferred adhesive coating weights will depend on adhesion parameters and adhesive factors such as desired degree of porosity and/or discontinuity, adhesive viscosity, tack, hot and cold flow, and molecular weigh. Adhesive coating weight may also depend on product design factors such as surface smoothness or roughness, surface absorption of adhesive, product size and weight and anticipated absorbent capacity.

Pressure sensitive adhesives that are not overly tacky and subject to excessive cold flow can be used. Preferred are adhesives and their formulations that have relatively low skin irritation potential, no skin sensitization potential and resistance to oxidation. So called "hypoallergenic" adhesives, such as the polyacrylates that have little or no potentially irritating antioxidants added, are examples of those that are preferred. These adhesives also have relatively good wet stick properties. Examples of adhesives other than polyacrylates, that can also be formulated to give low irritation potential, no sensitization potential and high oxidation resistance (but without being limited to these examples) are those based on: latex rubber, styrene-butadiene-styrene, styrene-isoprene-styrene and styrene-ethylene-butadiene-styrene.

The porous and/or discontinuous film can be coated and continuously from emulsion or solution directly on to the product substrate or on to a release substrate to be transferred on to the product substrate. Hotmelt adhesive coating, however, is preferred because of ease of manufacturing, no need for solvent removal and the ease of accomplishing and maintaining porosities, patterns and discontinuities in the film. Examples of such techniques for coating of such hotmelts are by hotmelt extrusion and spray, screen printing and gravure transfer coating. As shown in FIG. 2, a porous and/or discontinuous adhesive film 22 may also be used, if desired, to adhere perforate cover 25 to transfer layer 24. Similarly, if desired, transfer layer 24 may be adhered to absorbent core 12'. Nonporous, continuous adhesive coatings can also be coated directly onto the product surface or transferred from release surfaces onto those parts of the product that do not require porous coatings, by coating from emulsion, by solvent, by spraying or by knife coating. It can also be done from the hotmelt by extrusion, spraying, knife coating and by close patterned screen and gravure offset printing. Hotmelt adhesive coating is again preferred also for nonporous, continuous coatings for the reason given above the porous and/or discontinuous coatings. The nature, weight and coating techniques of applying adhesives 15 that adhere the barrier ply 14 to the core 12 where porosity is not absolutely necessary, i.e. those adhesives called "construction adhesives," are well known to those of ordinary skill in the art, and therefore will not be elaborated on herein, except to say that, if desired, adhesives or coating techniques identical to those for the body contacting adhesives 20, 20', 32 of this invention can also be used.

It has been found that, because of the small quantity of adhesive required for products in accordance with this invention, conventional release papers, usually used to cover and protect the adhesive until use, can be eliminated or substantially eliminated.

Figure 15:
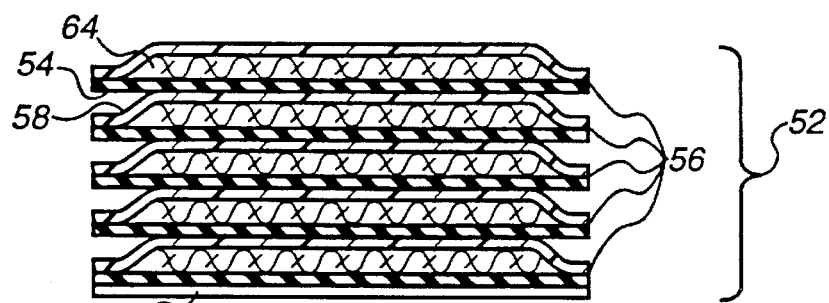
FIG. 15 is a cross-section of an assembly of multiple products in accordance with this invention.
Figure 16:
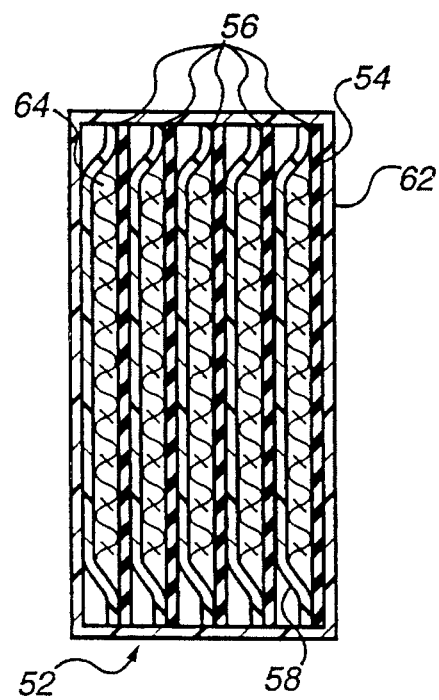
FIG. 16 is a cross-section of a package containing multiple products in accordance with the invention.

FIG. 15 shows an assembly of multiple products of this invention, generally designated by the reference numeral 52. The assembly 52 is depicted in FIG. 15 without the packaging material in which, it will be understood, it would ordinarily be presented. In such an assembly an adhesive coating 54 on the absorbent core 64 of one product 56 is placed in contact with the plastic barrier ply 58 of another product 56. The barrier ply 58 and adhesive coating 54 are disposed upon opposite surfaces of the absorbent core 64. Thus, it will be seen that release paper can be eliminated by stacking several products 56 face to back in a package, and only the adhesive coating 54 of the last product 56 to be used will require release paper 60. Even that release paper can be eliminated if, as is illustrated in FIG. 16, an overwrap 62 for the assembly 52 of products 56 is used to cover the adhesive coating 54 of the last product 56. The overwrap may be provided with an inner release surface to prevent adhesion to it of the last products' adhesive. Optionally, the inner surface of the overwrap 62 can be made of the same material as the barrier ply 58 or have the same release characteristics as barrier ply 58. No difficulty is encountered in peeling one product 56 away from its adherent neighbor; nor does adhesive transfer from one product to another.

Finally, it should be noted that the assembly of multiple products 58 need not be done in a single stack, as is illustrated in FIGS. 22 and 23. Products may be alternatively arranged in multiple stacks (not shown), wherein each stack has at least two products.

The present invention may be embodied in other specific forms without departing from its spirit or essential attributes. Accordingly, reference should be made to the appended claims, rather than the foregoing specification, for an indication of the scope of the invention.

What is claimed is:

1. An absorbent sanitary protection product for direct attachment to a user, the product having a periphery that defines it's outer border and surrounds it's center, the product comprising an absorbent core, a barrier ply coupled to said core on a side of said core away from the user, and a discontinuous adhesive layer operatively associated with said core and formed within the center of the product wherein at least a portion of the periphery is substantially free of adhesive between said core and the user and disposed to contact the user, said adhesive layer comprising pressure sensitive adhesive having sufficient adhesive strength to enable the product to adhere securely to the user and to be removed without pain or trauma to the user and permitting liquid to pass therethrough to said absorbent core.

2. An absorbent sanitary product in accordance with claim 1, wherein said adhesive layer comprises one or more of the following: polyacrylate, latex rubber, styrene butadiene styrene, styrene isoprene styrene and styrene ethylene butadiene styrene.

3. An absorbent sanitary product in accordance with claim 1, and a transfer layer abutting said absorbent core to facilitate transfer of liquid to said core, said adhesive layer being disposed on said transfer layer.

4. An absorbent sanitary product in accordance with claim 1, and a perforate cover abutting said absorbent core, said adhesive layer being disposed on said perforate cover.

5. An absorbent sanitary product in accordance with claim 1, a transfer layer abutting said core and a perforate cover abutting said transfer layer, and adhesive layer being disposed on said cover.

6. An absorbent sanitary product in accordance with claim 1, wherein said absorbent core comprises pulp and a binder.

7. An absorbent product in accordance with claim 6, wherein said binder comprises about fifteen percent (15%) by weight of said core.

8. The absorbent sanitary product in accordance with claim 1 wherein the adhesive strength is sufficient to enable the product to adhere to skin and hair of the user.

9. An absorbent sanitary product in accordance with claim 8 wherein said adhesive layer comprises an adhesive having low skin irritation potential, no sensitization potential and high oxidation resistance.

10. An absorbent product in accordance with claim 9, wherein said adhesive layer comprises a polyacrylate.

11. An absorbent sanitary product in accordance with claim 1, wherein said adhesive layer has a coating weight of about 0.5–15 mg./square inch.

12. An absorbent sanitary product in accordance with claim 11, wherein said adhesive layer has a coating weight of about 0.5–10 mg./square inch.

13. An absorbent sanitary product in accordance with claim 12, wherein said adhesive layer has a coating weight of about 0.5–5 mg./square inch.

14. An absorbent sanitary protection product for direct attachment to the skin and hair of a user, comprising a pad having a periphery that defines its outer border, an absorbent core, and a barrier ply coupled to said core on a side of said core away from the user, said pad when operatively disposed on the user covering substantially the entirety of the perineum of the user, a discontinuous adhesive layer associated with said pad and disposed between said absorbent core and said user and disposed to contact the user, said adhesive layer comprising pressure sensitive adhesive and permitting liquid to pass therethrough to said absorbent core, said pad having a narrowed posterior portion shaped to overlay the posterior labial commissure of a user but relieved to minimize contact between the pad and the buttocks.

15. An absorbent sanitary product in accordance with claim 14, wherein said adhesive layer has a coating weight of about 0.5–10 mg./square inch.

16. An absorbent sanitary product in accordance with claim 15, wherein said adhesive layer has a coating weight of about 0.5 to 5.0 mg./square inch.

17. An absorbent sanitary product in accordance with claim 14, wherein said pad, when operatively disposed on the user, extends beyond the anterior and posterior labial commissures by about 0.5 inches.

18. An absorbent sanitary product in accordance with claim 16, wherein said adhesive coating is disposed around the periphery of said pad, the center of said pad being substantially free of adhesive.

19. An absorbent sanitary product in accordance with claim 16, wherein said adhesive coating is disposed within the center of said pad, the periphery of said pad being substantially free of adhesive.

20. An absorbent sanitary product in accordance with claim 16, wherein a portion of the periphery of said pad is substantially free of adhesives to facilitate manual removal of said pad.

21. An absorbent sanitary product for direct attachment to skin and hair of a user, comprising a pad having an absorbent core and a barrier ply coupled to said core on a side of said core facing away from the user, said pad having a periphery that defines its outer border, at least one tab extending beyond said periphery, a discontinuous adhesive layer associated with said pad and said tab and being disposed between said absorbent core and said user and disposed to contact the user, said pad, when operatively disposed on the user, covering substantially the entirety of the perineum of the user, said pad being adapted, when operatively disposed, to contact the user beyond the perineum, said adhesive layer comprising pressure sensitive adhesive and permitting liquid to pass therethrough to said absorbent core, said pad having a narrowed posterior portion shaped to overlay the posterior labial commissure of a user but relieved to minimize contact between the pad and the buttocks.

22. An absorbent sanitary product in accordance with claim 21, wherein there are two said tabs, said tabs extending beyond said periphery and engaging the buttocks.

23. An absorbent sanitary product in accordance with claim 22, wherein said tabs engage the creases forming the juncture between the perineum and the inside of the thighs.

24. An absorbent sanitary product in accordance with claim 22, wherein said tabs engage the inside of the thighs.

25. An absorbent sanitary protection product for direct attachment to skin and hair of a user, comprising an absorbent core, a barrier ply coupled to said core on a side of said core away from the user, a discontinuous adhesive layer operatively associated with said core and formed between said core and disposed to contact the user, said adhesive layer comprising pressure sensitive adhesive having sufficient adhesive strength to enable the product to adhere securely to skin and hair of a the user and to be removed without pain or trauma to the user and permitting liquid to pass therethrough to said absorbent core, wherein a plurality of said products are stacked adjacent another and releasably coupled one to another with the adhesive layer of one product abutting the barrier ply of its neighboring product, whereby only one face of one of said products has its adhesive layer exposed.

26. An absorbent sanitary protection product in accordance with claim 25, wherein said exposed adhesive layer of said last product is covered with release paper.

27. An absorbent sanitary protection product in accordance with claim 25, wherein said multiplicity of products are enclosed in an overwrap.

* * * * *